United States Patent [19]

Mombrinie

[11] Patent Number: 4,923,187
[45] Date of Patent: May 8, 1990

[54] RADIOLUCENT ILIAC CREST SUPPORT FRAME

[75] Inventor: Bruno Mombrinie, Voorhees, N.J.

[73] Assignee: Avec Scientific Utility Corporation, Philadelphia, Pa.

[21] Appl. No.: 321,973

[22] Filed: Mar. 10, 1989

[51] Int. Cl.$^5$ ............................................. A61G 13/00
[52] U.S. Cl. ........................................ 269/328; 5/431
[58] Field of Search ................... 5/431, 437, 446, 432, 5/433, 436; 269/322–328; 378/208, 209

[56] References Cited

U.S. PATENT DOCUMENTS

| | | | |
|---|---|---|---|
| 4,571,757 | 2/1986 | Zolecki | 5/437 |
| 4,779,858 | 10/1988 | Saussereau | 378/209 |
| 4,796,315 | 1/1989 | Crew | 5/431 |

Primary Examiner—Robert C. Watson

[57] ABSTRACT

A radiolucent iliac crest support frame for supporting the iliac crest of a person and maintaining the person's spine in a substantially straight horizontal position is disclosed. The support frame comprises a radiolucent sheet, means for causing the sheet to grip the horizontal surface when the sheet is placed on the surface, means for supporting the iliac crest of a person above the sheet and for maintaining the person's spine in a substantially straight horizontal position, and means for adjustably attaching the supporting means to the radiolucent sheet. The supporting means preferably are two oblong radiolucent pillows adjustably attached to the sheet by means of fastener pads and strips whereby the position of the pillows can be adjusted to accommodate patients of different sizes.

14 Claims, 1 Drawing Sheet

RADIOLUCENT ILIAC CREST SUPPORT FRAME

BACKGROUND OF THE INVENTION

The invention is principally directed to the area of medical operations and examination involving human patients. Particularly, the invention is directed to applications involving back surgery or x-ray examination of the back of the patient.

In most humans, the spinal column is curved. The natural curvature of the spine makes back surgery involving the vertebrae difficult since the vertebrae are forced closer together by the curvature. Similarly, the spinal curvature makes x-ray examination difficult because the vertebrae are not aligned in a straight line but rather follow the curvature of the spine.

The ability to maintain the spine in a straight, uncurved position would facilitate back surgery procedures and x-ray examination procedures. However, heretofore, no apparatus for effectively maintaining the spinal column in a straight, aligned position, which apparatus is also essentially transparent or at least substantially transparent to x-rays (i.e. radiolucent), to permit effective x-ray examination of the spinal column has been available.

SUMMARY OF THE INVENTION

The invention encompasses a support device for maintaining the spine in a substantially uncurved position during surgery or x-ray examination.

The "iliac crest", as used in this application refers to the upper edge of the pelvis.

The invention embraces a radiolucent iliac crest support frame for supporting the iliac crest of a person and maintaining the person's spine in a substantially straight horizontal position, comprising:
a. a radiolucent sheet;
b. means for causing the sheet to grip a horizontal surface when the sheet is placed on said surface;
c. means for supporting the iliac crest of a person above the sheet; and
d. means for adjustably attaching said means for supporting to the radiolucent sheet.

The invention also embraces a radiolucent iliac crest support frame for supporting the iliac crest of a person and maintaining the person's spine in a substantially straight horizontal position, comprising:
a. a radiolucent sheet;
b. two rubber strips attached to a first surface of said sheet wherein the rubber strips are in parallel with each other and at opposite ends of the first surface;
c. two fastener strips attached to a second surface of said sheet wherein the second surface is on a side opposite the first surface of the sheet and wherein the fastener strips are oriented on the second surface in substantially the same orientation as the rubber strips on the first surface, each fastener strip being located opposite a rubber strip on the other surface of the sheet; and
d. two oblong radiolucent pillows adjustably attached to the second surface of the sheet so that the pillows are oriented parallel to the second surface and perpendicular to the fastener strips and wherein each pillow has two fastening pads on a side of the pillow closest to the fastener strips and at opposite ends of that side and wherein the fastener strips and the fastening pads cooperate to adjustably attach the pillows along the fastening strips.

DETAILED DESCRIPTION OF PREFERRED EMBODIMENTS

Figure 1:
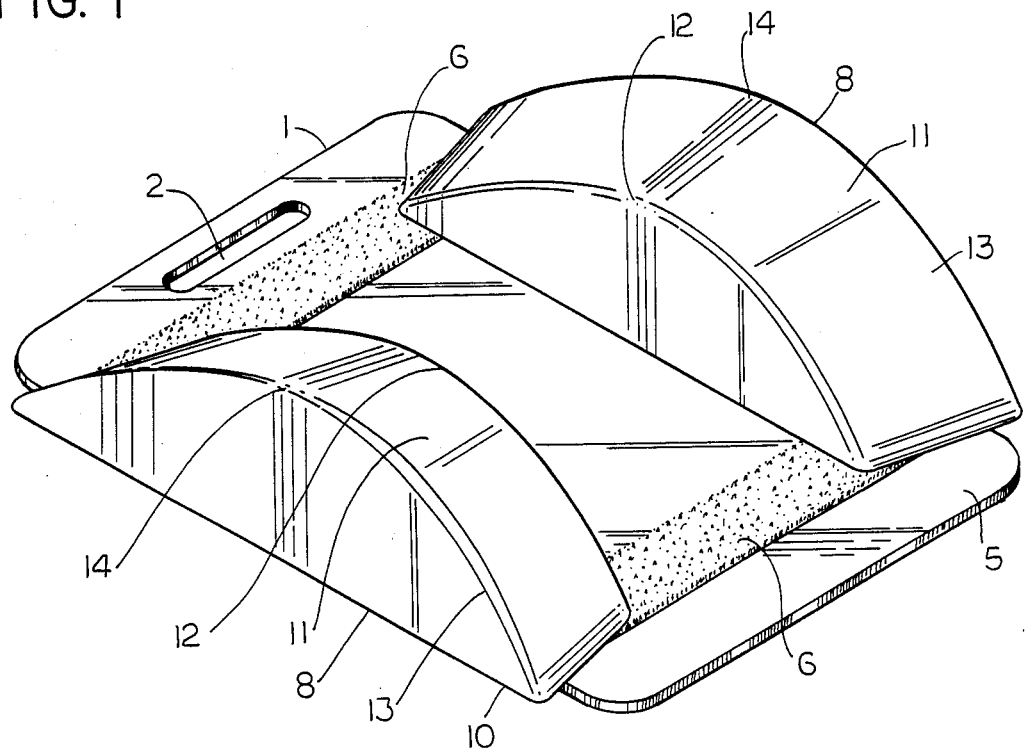
FIG. 1 is a top view of applicant's radiolucent support apparatus.
Figure 2:
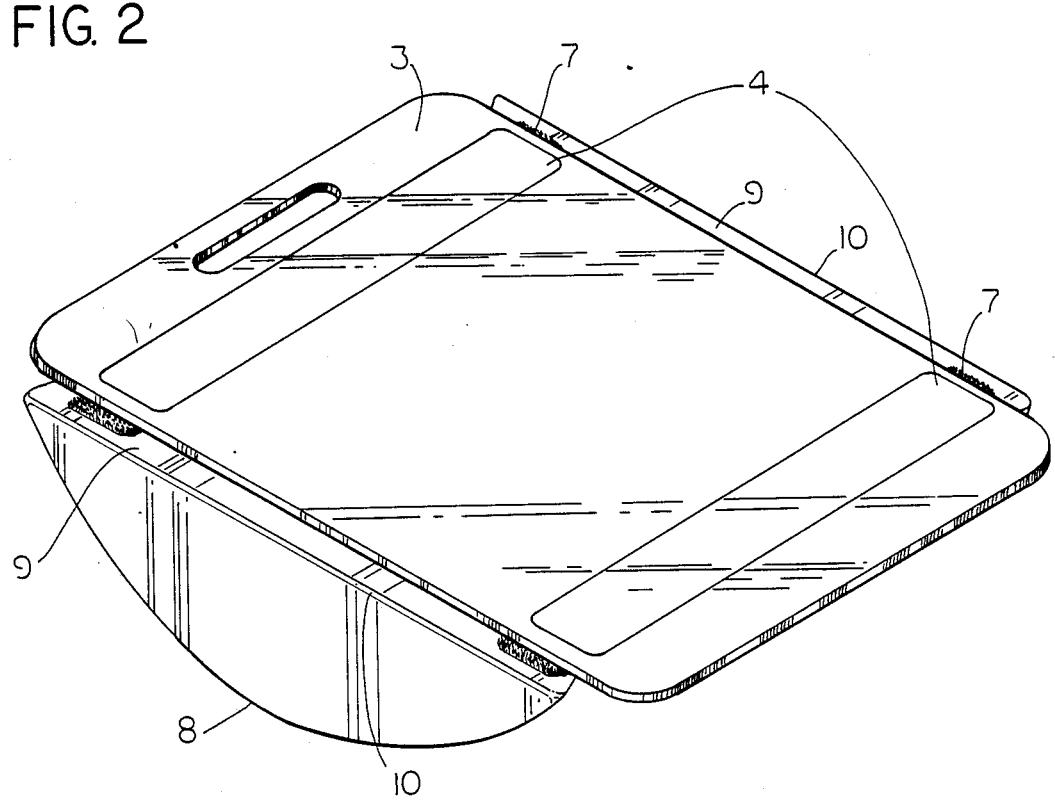
FIG. 2 is an underside view of the radiolucent support apparatus shown in FIG. 1.

FIGS. 1 and 2 illustrate a preferred embodiment of the apparatus of the invention.

The apparatus comprises an sheet 1 which is radiolucent (i.e. x-ray transparent). The sheet 1 may contain a perforation 2 at one end to serve as a handle for carrying the apparatus.

On the underside (the first planar surface) 3, there are attached two rubber strips 4. The these rubber strips 4 are preferably oriented parallel to one another and located at opposite ends of the underside 3 of the sheet. The rubber strips 4 prevent the sheet 1 from slipping or sliding during use (for example when the apparatus is placed on an operating table or an x-ray examination table).

On the top side 5 of the sheet (the second planar surface), there are two straight, parallel, substantially constant and equal width fastener strips 6. The strips 6 are preferably positioned towards opposite ends of the sheet. They are preferably parallel to one another and occupy the same relative positions as the rubber strips 4 on the underside 3 of the sheet. The fastener strips 6 are preferably male velcro type fasteners. The fastener strips 6 cooperate with fastening pads 7 to fix the support pillows 8 in place on the sheet 1.

The apparatus includes two pillows 8 which are formed from a radiolucent material. The pillows 8 are shaped to allow the spine to be in a substantially straight horizontal position when the iliac crest of the patient is positioned on the pillows 8 and the patient is prone face down.

The lower side (first side) 9 of each pillow preferably is flat and has a trapezoidal shape. The pillows 8 are preferably oriented parallel to one another and perpendicular to the fastener strips 6 on the top surface 5 of the sheet. The pillows 8 are oriented on top surface 5 of the sheet so that the base (widest) edges 10 of the trapezoidal surfaces 9 (i.e. the underside) are furthest from each other.

The top side 11 of each pillow is curved and sloped downward toward the center of the sheet 1. The top side 11 of each pillow has a frustoconical shape. (A frustoconical shape is formed by removing the vertex portion from a cone. The remaining portion, with the vertex removed, is the frustoconical portion.)

The edge 12 of the frustoconical side having the smallest radius of curvature is closest to the center of the sheet 1 whereas the opposite edge 13 having the largest radius of curvature is located furthest from the center of the sheet 1. The top side 11 of the pillow slopes downwardly from the outside edge 13 toward the inside edge 12 or toward the center of the sheet 1.

On the underside 9 of the pillows, fastening pads 7 are attached to the pillow 8 toward opposite ends of that side 9. The separation distance between the fastening pads 7 on a pillow 8 is approximately equal to the distance between the fastening strips 6 on the top surface 5 of the sheet. The fastening pads 7 cooperate with the fastening strips 6 to adjustably attach the pillows 8 to the top surface 5 of the sheet. The fastening pads 7 are preferably female velcro material. It is understood that the invention also encompasses the embodiment wherein the fastener strips 6 are female and the fastening pads 7 are male or any other functioning combination of male and female type fasteners.

The relative position of the pillows 8 may be adjusted by prying lose the fastening pads 7 from the fastening strips 6 on the sheet 1.

In using the radiolucent support apparatus of the invention for back x-rays or back surgery, the patient is positioned so that the iliac crest (upper edge of the pelvis) of the patient rests on the apex 14 of the pillows. The person is positioned lying parallel to the pillows 8 (the pillows preferably being parallel to each other) and in the face down prone position. With this positioning, the spine will remain substantially straightened and the vertebrae drawn apart facilitating either x-ray examination or back surgery.

Using the support frame apparatus of the invention, the patient is typically elevated above the sheet 1 leaving a space between the patient and the sheet 1. This elevated position facilitates drainage of blood and other body fluids which may be exuded during surgery. In one preferred embodiment, a container is placed on the sheet 1 underneath the patient to collect body fluids during surgery.

The pillows 8 are formed preferably from a low density, low molecular weight, open-cell polyurethane foam. The foam pillow is preferably dipped in a liquid phase elastomeric material which coats the foam pillow and forms a skin. The foam preferably has a firmness rating of about 35 to 45 I.L.D. and a density of about 1.8 lbs. per cubic foot. The elastomeric coating on the pillow is preferably PDC-10 (manufactured by PDI, Inc. of St. Paul, Minnesota) which consists primarily of 1, 1, 1-trichloromethane, methylene chloride, petroleum distillates and toluene. The degree of slope on the upper side 11 of the pillow is not critical, however, preferably some slope is present.

The sheet may be formed from any acrylic plastic or other suitable material which is radiolucent and has the necessary mechanical strength and degree of inertness.

While the invention has been discussed with respect to the preferred embodiment, it is understood that other modifications such as changes in materials used, pillow shape or fastening mechanisms can be used and are within the scope of the invention.

I claim:

1. A radiolucent iliac crest support frame for supporting the iliac crest of a person and maintaining the person's spine in a substantially straight horizontal position, comprising:
   a. a radiolucent sheet;
   b. means for causing the sheet to grip a horizontal surface when the sheet is placed on said surface;
   c. means for supporting the iliac crest of a person above the sheet and maintaining said person's spine in a substantially straight horizontal position;
   d. means for adjustably attaching said means for supporting and maintaining to the radiolucent sheet.

2. A radiolucent iliac crest support frame for supporting the iliac crest of a person and maintaining the person's spine in a substantially straight horizontal position, comprising:
   a. a radiolucent acrylic sheet;
   b. two flat rubber strips attached to a first planar surface of said sheet wherein the rubber strips are in parallel with each other and at opposite ends of the first planar surface;
   c. two male velcro fastener strips attached to a second planar surface of said sheet wherein the second planar surface is on a side opposite the first planar surface of the sheet and wherein the male velcro strips are oriented on the second planar surface in the same orientation as the rubber strips on the first planar surface, each male velcro strip being located opposite a rubber strip on the other planar surface of the sheet;
   d. two radiolucent, oblong, low density, low molecular weight polymer foam pillows adjustably attached to the second planar surface so that the pillows are oriented parallel to the second planar surface and perpendicular to the male velcro strips and wherein
      i. each pillow has a first side closest to the sheet which first side is planar and has a trapezoidal shape and a second side opposite the first side which second side is in the shape of a surface of a portion of a frustoconical section oriented so that the frustoconical surface has a smaller radius of curvature closer to the other pillow and a larger radius of curvature further from the other pillow; and
      ii. each pillow has female velcro fasteners located at opposite ends on the first side of the pillow so that each pillow may be oriented on the second planar surface with the male velcro fasteners engaging the female velcro fasteners; and
   e. a hole near one edge of said sheet such that a portion of the sheet between the hole and the edge serves as a handle for carrying the frame.

3. A radiolucent iliac crest support frame for supporting the iliac crest of a person and maintaining the person's spine in a substantially straight horizontal position, comprising:
   a. a radiolucent sheet;
   b. two rubber strips attached to a first surface of said sheet wherein the rubber strips are in parallel with each other and at opposite ends of the first surface;
   c. two fastener strips attached to a second surface of said sheet wherein the second surface is on a side opposite the first surface of the sheet and wherein the fastener strips are oriented on the second surface in substantially the same orientation as the rubber strips on the first surface, each fastener strip being located opposite a rubber strip on the other surface of the sheet; and
   d. two oblong radiolucent pillows adjustably attached to the second surface of the sheet so that the pillows are oriented parallel to the second surface and perpendicular to the fastener strips and wherein each pillow has two fastening pads on a side of the pillow closest to the fastener strips and at opposite ends of that side and wherein the fastener strips and the fastening pads cooperate to adjustably attach the pillows along the fastening strips.

4. The frame of claim 3 wherein the pillows contain a low density, low molecular weight polymer foam.

5. The frame of claim 3 wherein the sheet is an acrylic plastic sheet.

6. The frame of claim 3 wherein the sheet contains a hole near one edge and a portion of the sheet between the hole and the edge serves as a handle for carrying the frame.

7. The frame of claim 3 wherein the fastener strips are male velcro fasteners and the fastening pads are female velcro fasteners.

8. The frame of claim 3 wherein there is a space between the pillows where a container for collecting body fluids may be placed.

9. A radiolucent iliac crest support frame for supporting the iliac crest of a person and maintaining the person's spine in a substantially straight horizontal position, comprising;
   a. a radiolucent sheet;
   b. two rubber strips attached to a first surface of said sheet wherein the rubber strips are in parallel with each other and at opposite ends of the first surface;
   c. two fastener strips attached to a second surface of said sheet wherein the second surface is on a side opposite the first surface of the sheet and wherein the fastener strips are oriented on the second surface in substantially the same orientation as the rubber strips on the first surface, each fastener strip being located opposite a rubber strip on the other surface of the sheet; and
   d. two radiolucent oblong pillows adjustably attached to the second surface so that the pillows are oriented parallel to the second surface and perpendicular to the fastener strips and wherein
      i. each pillow has a first side closest to the sheet which first side is planar and has a trapezoidal shape and a second side opposite the first side which second side has the shape of a surface of a portion of a frustoconical section oriented so the frustoconical surface has a smaller radius of curvature closer to the other pillow and a larger radius of curvature further from the other pillow; and
      ii. each pillow has two fastening pads on the first side of the pillow at opposite ends of that side and wherein the fastener strips and the fastening pads cooperate to adjustably attach the pillows along the fastening strips.

10. The frame of claim 9 wherein the pillows contain a low density, low molecular weight polymer foam.

11. The frame of claim 9 wherein the sheet is an acrylic plastic sheet.

12. The frame of claim 9 wherein the sheet contains a hole near one edge and a portion of the sheet between the hole and the edge serves as a handle for carrying the frame.

13. The frame of claim 9 wherein the fastener strips are male velcro fasteners and the fastening pads are female velcro fastener.

14. The frame of claim 9 wherein there is a space between the pillows where a container for collecting body fluids may be placed.

* * * * *